United States Patent
O'Donnell, Jr.

[11] Patent Number: 6,080,144
[45] Date of Patent: Jun. 27, 2000

[54] METHOD OF IMPROVING PHOTOREFRACTIVE KERATECTOMY BY INCREASING ABLATION SMOOTHNESS

[76] Inventor: Francis E. O'Donnell, Jr., 709 The Hamptons La., Town and Country, Mo. 63017

[21] Appl. No.: 08/901,323

[22] Filed: Jul. 28, 1997

Related U.S. Application Data

[60] Provisional application No. 60/022,733, Jul. 29, 1996.

[51] Int. Cl.⁷ ..................................................... A61M 5/06
[52] U.S. Cl. ...................................... 606/5; 606/3; 606/10
[58] Field of Search ................................. 606/3–7, 10–14

[56] References Cited

U.S. PATENT DOCUMENTS

| | | | |
|---|---|---|---|
| 4,669,466 | 6/1987 | L'Esperance | 606/11 |
| 4,784,135 | 11/1988 | Blum et al. | |
| 4,941,093 | 7/1990 | Marshall et al. | |
| 5,123,902 | 6/1992 | Müller et al. | 606/5 |
| 5,144,630 | 9/1992 | Lin | |
| 5,163,934 | 11/1992 | Munnerlyn | 606/13 |
| 5,492,135 | 2/1996 | De Vore et al. | 128/898 |
| 5,520,679 | 5/1996 | Lin | |

FOREIGN PATENT DOCUMENTS 280414  8/1988  European Pat. Off. ................... 606/5

*Primary Examiner*—David Shay
*Attorney, Agent, or Firm*—Paul M. Denk

[57] ABSTRACT

A method of performing photorefractive keratectomy (PRK) wherein the surface smoothness is enhanced. The present invention minimizes the ablation zone dimension including central ablation depth, reducing the need for overcorrection. The present invention reduces regression and scarring (haze) providing enhanced clinical outcomes with faster rehabilitation, greater refractive stability, and improved corneal clarity. Moreover, improved clinical outcomes are achieved by adjusting the initial corneal correction to take into account the effects of regression based upon non-linear predictive formulas which vary with the square of the slope of ablation smoothness (roughness) per micron of ablation depth.

1 Claim, 6 Drawing Sheets

| SAMPLE | PV(nm) | RAMS(nm) | Ra(nm) |
|---|---|---|---|
| SINGLE PASS(1X-6.0D | | | |
| WITHOUT MOTION | 5159.82 | 342.66 | 250.22 |
| WITH MOTION | 2127.70 | 277.04 | 215.96 |
| MULTIPLE PASS(3X-2.42 | 3913.42 | 313.44 | 247.05 |
| WITHOUT MOTION | 3913.42 | 313.44 | 247.05 |
| WITH MOTION | 3077.52 | 323.98 | 247.56 |

TABLE 1: ROUGHNESS DATA FOR SINGLE PASS AND MULTIPLE PASS ABLATIONS WITH AND WITHOUT MOTION.

METHOD OF IMPROVING PHOTOREFRACTIVE KERATECTOMY BY INCREASING ABLATION SMOOTHNESS

CROSS-REFERENCE TO RELATED APPLICATION

This application claims priority on the provisional application filed on Jul. 29, 1996, under Ser. No. 60/022,733, of the same applicant.

BACKGROUND OF THE INVENTION

This invention relates to photorefractive keratectomy (PRK) and, in particular, to a method of performing PRK to increase ablation smoothness.

Blum (U.S. Pat. No. 4,784,135) taught the use of pulsed ultraviolet lasers with output in the 200 nm or less range (e.g., argon fluoride excimer laser) for the purpose of photodecomposition (photoablation) of organic living tissue. Others, such as Munnerlyn (U.S. Pat. No. 5,163,934) and Marshall (U.S. Pat. No. 4,941,093), taught the use of variable aperture (iris diaphragm) delivery system with the excimer laser to photoetch (sculpt) a lens shape on the human cornea for the correction of refractive errors. Lin (U.S. Pat. No. 5,520,679) taught the use of small, overlapping pulses delivered in a scanning mode, showing that the corrective lens contour could be achieved without resorting to high power lasers required in variable aperture systems. Moreover, Lin taught (U.S. Pat. No. 5,144,630) alternate sources of pulsed UV, such as solid state, and he taught the use of infrared for PRK.

Clinical experience with photorefractive keratectomy (PRK) has demonstrated a problem with a lack of stability, inaccuracy, and a tendency toward scar formation (subepithelial haze) with larger corrections. This was attributed erroneously to a more vigorous healing response with deeper ablations into the stroma. Therefore, so-called "multizone techniques" were introduced to achieve larger corrections with shallower ablations. Unfortunately, this has meant limiting the full correction to a relatively small central part of the ablation (treatment) zone on the cornea. Unwanted side effects include monocular diplopia, ghosting and halos from pupil dilation in scotopic conditions such as night driving.

I have determined that ablation smoothness rather than ablation depth per se is the key to enhancing the clinical results of PRK.

This current invention comprehends a series of simulated PRK in polymethylmethacrylate (PMMA) or other material and then analyzing the surface smoothness of the treated target using a scanning white light interferometer. There is an inverse linear relationship generated between the ablation depth, and the surface smoothness. From Munnerlyn, it was known that ablation depth was linearly related to the refractive correction, and that it varied with the square of ablation diameter. Prior to this current study, it does not appear that anyone has demonstrated the relationship between the ablation depth, and the surface roughness. This principle applies to ablation of cornea, as well as to ablation with the UV laser or infrared laser. Using this determination, a better understanding of the effects of PRK on the human cornea, and what modifications need to be made to the laser hardware and software, does provide an enhanced effect upon the ablation smoothness. This is to say, for the same ablation depth, modifications to the laser hardware and software dramatically alter the ablation smoothness. For the first time, I have determined that ablation smoothness, in turn, affects the ablation anatomy required to yield satisfactory outcome. Rough surfaces stimulate more regression (and haze) as a result of the reparative response of the cornea to fill in the surface irregularities. Therefore, a rough ablation surface requires an overshoot of the desired final refractive correction in order to take into account the effects of regression. This means that a deeper ablation must be done to compensate for a rough ablation surface. This further exacerbates the surface roughness because of the linear relationship between ablation depth and ablation roughness. By employing a variety of techniques, one is able to show increased ablation smoothness for a given correction through usage of any laser of the photorefractive keratectomy (PRK) operation, whether ultraviolet or infrared, and whether variable aperture or scanning is involved. Furthermore, one can identify minimal acceptable performance standards utilizing a standardized PMMA test target. A root means square (RMS) value below 15 nm per micron of ablation depth, for example, is required to achieve reasonable accuracy, stability, and corneal clarity for six diopter or less correction. There is a nonlinear relationship between RMS per micrometer and the initial correction in cornea necessary to compensate for regression. That is to say, there is a need to overcorrect (overshoot) the desired refractive result if the treatment results in a surface roughness in excess of a threshold amount. A best-fit plot based upon RMS measurements provides a means to predict the initial central corneal ablation depth necessary to take into account the adverse effects of regression.

SUMMARY OF THE INVENTION

It is, therefore, a principal object of this invention to provide a method of performing photorefractive keratectomy wherein the surface smoothness is enhanced in order to provide greater accuracy, better stability, and increased clarity of the cornea.

Another object of the present invention is to provide enhanced surface smoothness so as to reduce the need to overshoot the targeted correction (overcorrect), by reducing the potential for regression.

Still another object of this invention is to provide a method wherein the targeted correction is fractionated into multiple cycles of a smaller correction.

Still another object of this invention is to provide a method of energy homogenizing means which are used to enhance ablation smoothness.

Yet another object of this invention is to provide a method of usage of a masking solution or substance on the target surface to provide a smoother ablation profile.

Yet another object of this invention is to provide a method wherein the target tissue, or focusing optics of the delivery system, are imparted with a slight vibratory motion to smooth the ablation surface.

Yet another object of this invention is to provide a method wherein the fluenuce at the cornea surface is lower to enhance ablation smoothness.

Still another object of this invention is to provide a method wherein the laser is defocused so as to smooth the ablation surface.

Yet another object of this invention is to provide a method wherein the target tissue is kept reasonably hydrated, but not excessively so, in order to enhance the ablation smoothness.

Still another object of this invention is to provide a method wherein the cornea surface is cooled to below 80° F. to reduce thermal-induced irregularity on the corneal surface.

Yet another object of this invention is to provide a method wherein a scanning spot delivery system is used to provide a smoother ablation surface than a variable aperture delivery system.

Yet another object of this invention is to provide a method wherein the laser is used to remove successive scanned layers by rotating the direction of succeeding scans 60°–90° in order to enhance ablation smoothness.

Yet another object of this invention is to provide the method wherein the laser rotates the scanned layer direction randomly between 30° and 90° in order to enhance ablation smoothness.

Still another object of this invention is to provide a method wherein the extent and pattern of pulsed overlap is modified to enhance the ablation smoothness of the laser treatment.

Another object of this invention is to provide a method wherein the ablation profile is aspheric so as to reduce central ablation depth in order to increase ablation smoothness.

Yet another object of this invention is to provide a method wherein a contact lens is used temporarily after the treatment to enhance surface smoothness.

Still another object of this invention is to provide the method wherein a means of surface profilemetry is used to determine parameters of surface smoothness, such as peak-to-valley (PV), roof means square (RMS) and arithmetic average (R.A.).

Yet another object of this invention is to provide the method wherein the surface profile meter is a scanning white light interferometer.

Still another object of this invention is to provide the method wherein the surface profile meter is a contact profile meter.

Yet another object of this invention is to provide the method wherein the measure of ablation smoothness divided by the ablation depth is a standardized test material or in human cornea is expressed as a unit used to identify minimal acceptable performance standards of ablation smoothness.

Yet another object of this invention is to provide the method wherein the RMS measurement in nanometers per micron of ablation depth in a standardized PMMA and is less than 15.

Another object of this invention is to provide the method wherein the PV measurement in nanometers per micron of ablation depth in a standardized PMMA is less than 90.

Finally, another object of this invention is to provide the method wherein the RA measurement in nanometers per micron of ablation depth in a standardized PMMA is less than 10.

Yet another object of this invention is to use the linear relationship between ablation roughness and ablation depth to predict the non-linear relationship targeted correction in cornea necessary to take into account the effects of regression. In the case of RMS, for example, the initial corneal correction in microns of central ablation depth $ho^1$ is approximated by the non-linear formula: $ho^1 = 0.078\ AN^2 + ho$, where AN is equal to the slope of the plot of RMS as a function of ablation depth, ho is the central ablation depth of the targeted refractive correction (i.e., the desired correction), and $ho^1$ is the targeted correction.

Other objects and purposes will become more apparent to those skilled in the art upon reviewing this summary of the invention, and the description of the preferred embodiment provided herein in view of the drawings.

DESCRIPTION OF THE PREFERRED EMBODIMENT

The present invention relates to the selection of hardware and software combination that show a demonstrably smoother ablation for a given ablation depth. In addition, modifications at the target tissue can be used to enhance smoothness. By using these embodiments of the present invention which provide a smoother ablation surface, the ablation zone anatomy can be minimized (reducing the need to overcorrect) and the refractive result is more accurate, more stable with greater clarity.

Figure 6:
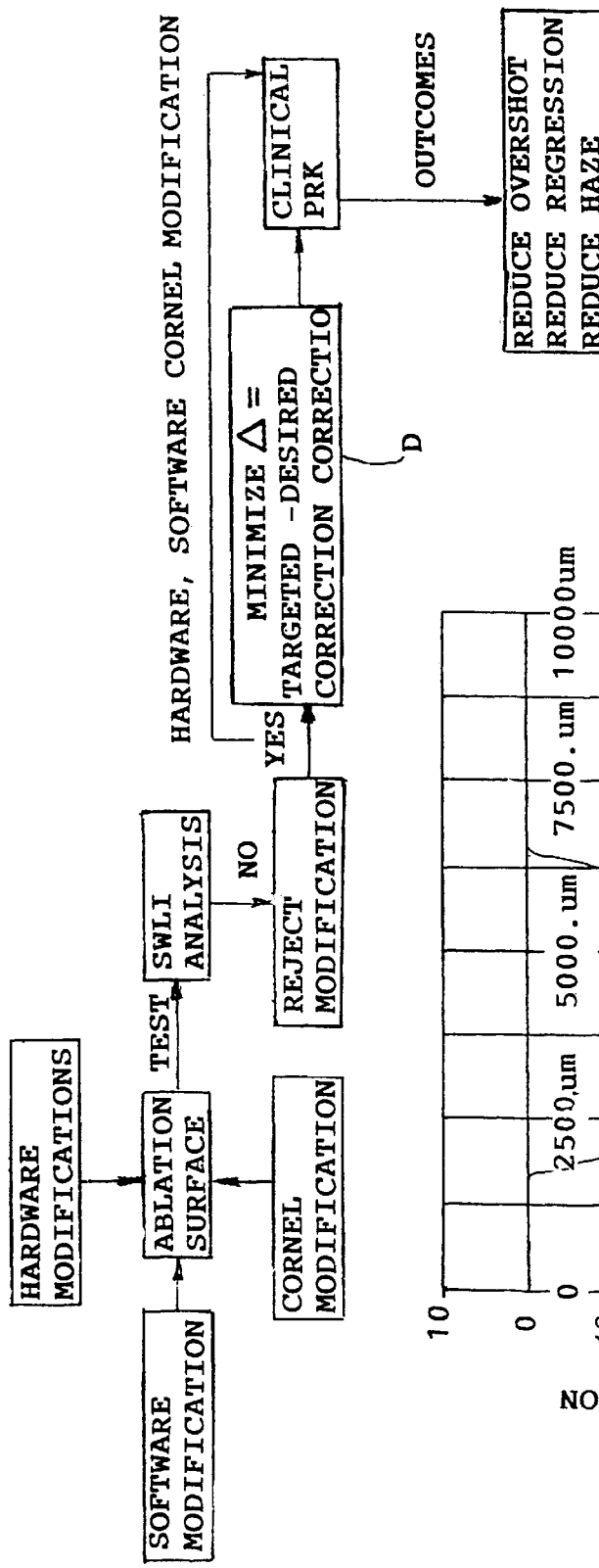
FIG. 6 is a block diagram of the method for choosing a combinations of improvements in hardware and software to increase the smoothness of the ablation surface.

In a preferred embodiment of the present invention, the improvements in hardware, software, and corneal surface are employed in an effort to increase the smoothness of the ablation surface. This method is shown in FIG. 6. A selected set of modifications are tested by performing ablations on simulated corneal surfaces, such as a polymethylmethacrylate (PMMA) or cross-linked collagen. The ablation is then analyzed using scanning white light interferometer (SWILL) analysis. If the ablation smoothness is not improved by the proposed modifications, the proposed modification in the hardware, software, or corneal surface is rejected. If the modification results in an improved surface smoothness, than the modification is used to reduce the difference between the targeted correction and the desired correction. The targeted correction is calculated using the formula: $ho^1 = 0.078\ AN^2 + ho$, where AN is equal to the slope of the plot of RMS as a function of ablation depth, ho is the central ablation depth of the targeted refractive correction (i.e., the desired correction), and ho$^1$ is the targeted correction. The difference between ho$^1$ and ho is calculated at block D in the diagram. As the difference delta ($\Delta$) between ho$^1$ and ho decreases, the ablation smoothness increases.

By increasing ablation smoothness, the present invention reduces the need to overcorrect because of effects of regression. By reducing the need to overcorrect, it is possible to make the targeted correction more closely equal to the desired correction. This change in the targeted correction is entered into the PRK laser and the appropriate improvement (hardware, software, or corneal surface modification) is utilized in the PRK procedure. The present invention results in improved outcomes as measured by reduced overshoot, reduced regression, and reduced subepithelial haze.

In one preferred improvement, variable aperture lasers for photorefractive keratectomy are used to perform PRK wherein the treatment is fractionated into multiple repetitive cycles. For example, a minus twelve is fractionated into four cycles of a minus three. I have determined that this causes a smoother profile by reducing the ridges associated with the stop positions of the iris diaphragm delivery system. This is shown in Table I below.

TABLE I

| Excimer Delivery System | Targeted Correction for cornea | Measured Central Ablation Depth in PMMA |
| --- | --- | --- |
| Variable aperture with beam homogenizer | −6.00 diopter | 42 microns |
| Variable aperture without beam homogenizer | −6.00 diopter | 72 microns |

The effects of ablation smoothness on the required ablation zone anatomy to achieve the same refractive correction in a living eye. Note that the smoother ablating excimer delivery system with beam homogenizer requires a more shallow ablation depth as measured by contact profilemetry in polymethylmethacrylate (PMMA) than does the delivery system without beam homogenizer.

Figure 1:
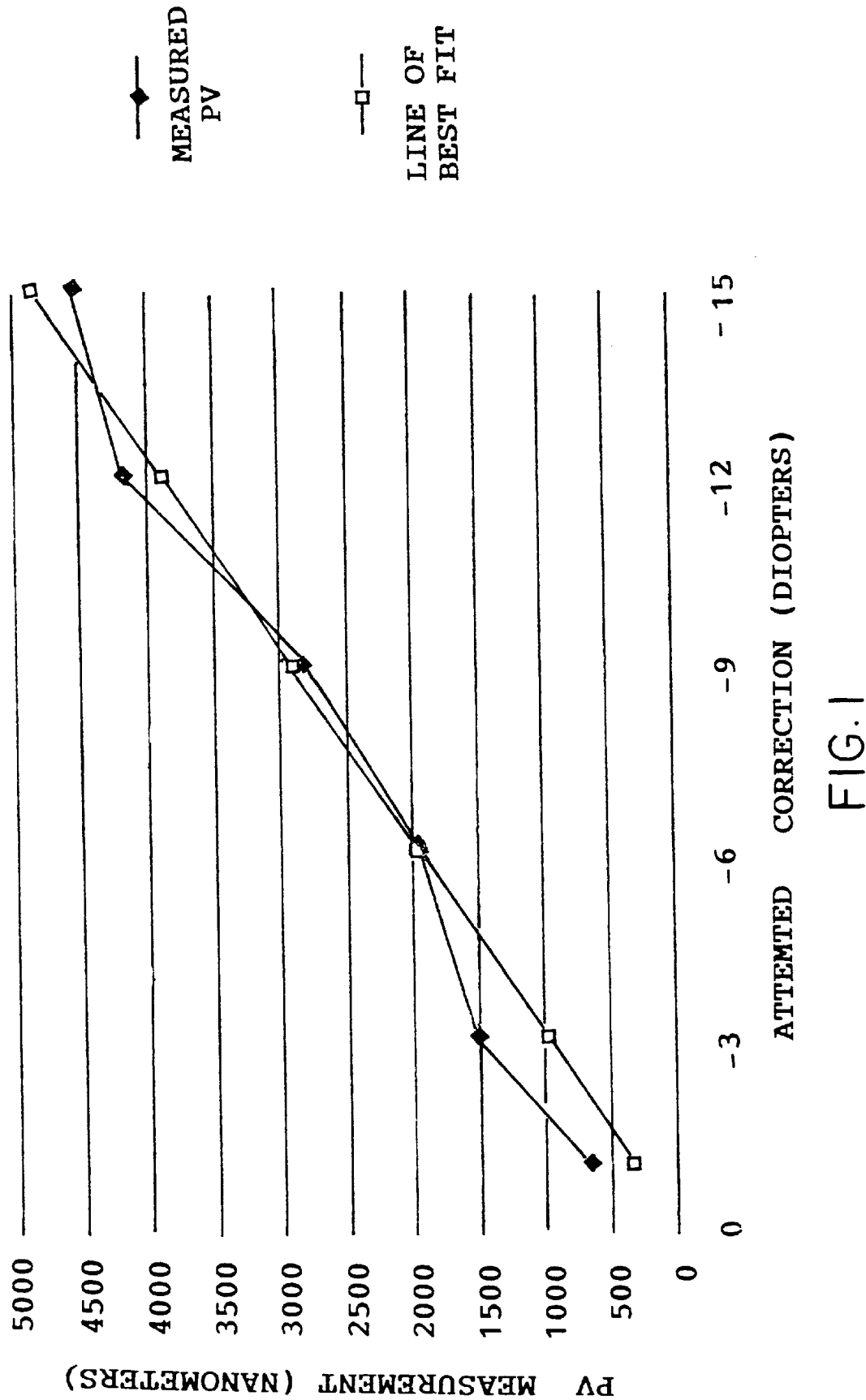
FIG. 1 is a plot of attempted correction (in diopters) in standardized polymethylmethacrylate test substrate against the resultant surface smoothness as measured with a scanning white light interferometer; it is a plot, a parameter of surface smoothness called "PV" (peak-to-valley) in nanometers in usage. There is a linear relationship between the attempted targeted correction and the effect on surface smoothness as noted in this figure.
Figure 2:
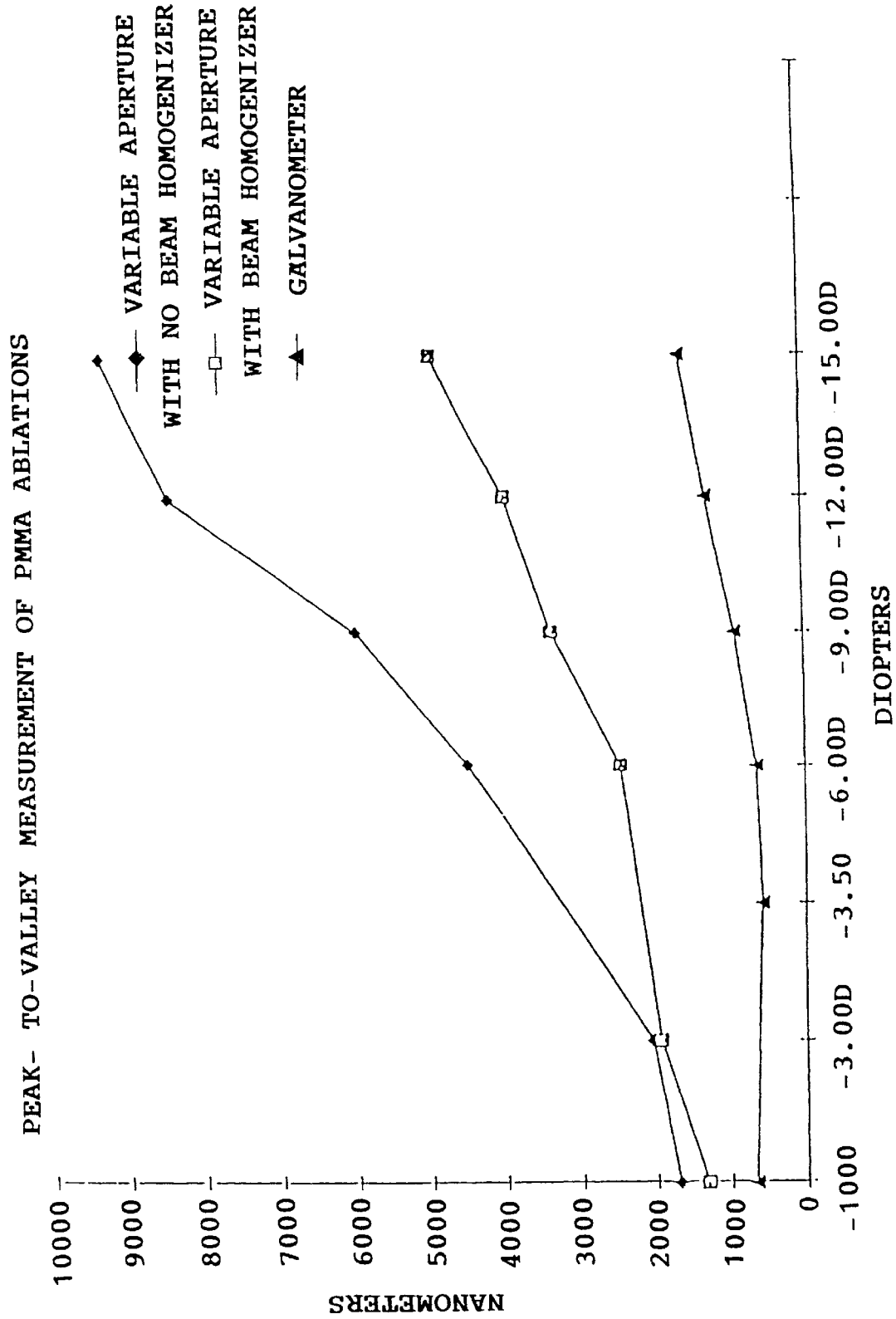
FIG. 2 provides the effects of differences in laser delivery systems on surface smoothness in standardized polymethylmethacrylate; noting that variable aperture system with no beam homogenizing mechanism provides a relatively rough ablation surface in comparison to a variable aperture system with beam homogenizer, which in turn, the galvanometric scanning delivery system provides an even smoother ablation profile for each targeted correction, as noted.

In another embodiment for variable aperture system, a beam homogenizing mechanism such as a rotating K-mirror, energy filter, or spatial integrator is used to reduce the uneven energy distribution across the beam profile. I have determined that this enhances the ablation smoothness for the same ablation depth. Tests results are shown in FIG. 2.

In another preferred embodiment for a variable aperture system, a slightly viscous solution such as sodium hyaluronate is applied to the surface after the corrective lens is sculpted. Then, with an open diaphragm, an additional 1–2 microns of tissue and "masking solution" is removed. This results in a smoother ablation surface by removing the "peaks" in the target tissue while shielding the "valleys."

Figures 3, 4A:
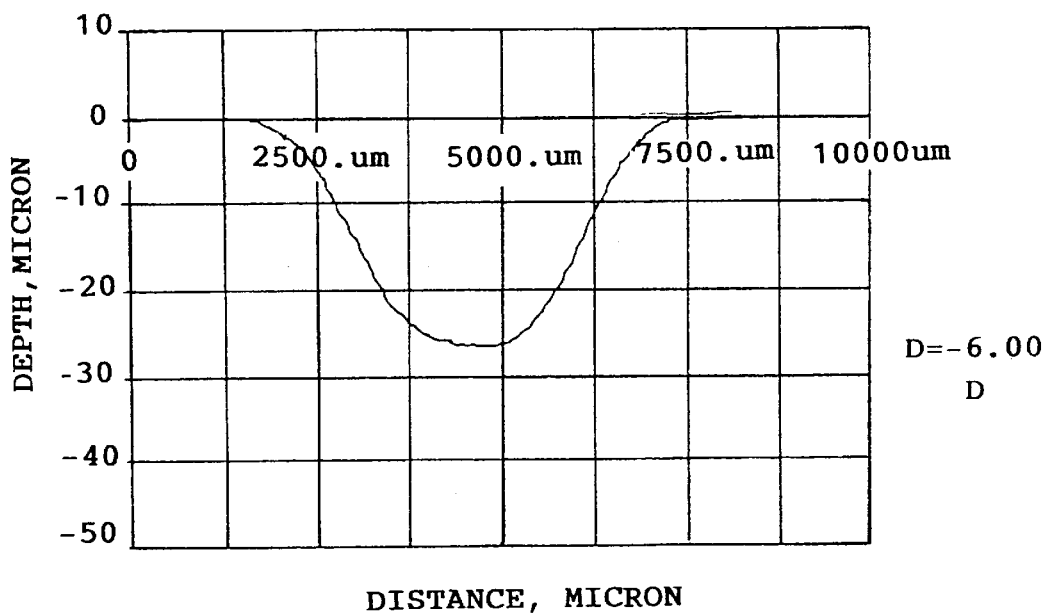
FIG. 3 discloses the roughness (smoothness) data for a single pass and multiple (fractionated) pass ablations with and without vibratory motion.

In another preferred embodiment for variable aperture systems, I have provided a slight vibratory motion to the target to reduce the surface roughness (FIG. 3). By using a vibrating device attached to the index finger and by gently placing the top of the surgeon's index finger on the target during the PRK, the ablation smoothness is enhanced. Alternatively, the laser optics, or a component thereof, can be vibrated slightly.

In another preferred embodiment, the fluence of the variable aperture system is lowered so that it is suprathreshold, but not excessively. For example, if the fluence is reduced from 180 mJ/cm$^2$ to 110 mJ/cm$^{2}$, the surface smoothness is enhanced by reducing the etch rate per pulse.

In another preferred embodiment, the variable aperture system is defocused so as to blur the etching of the iris stop positions on the target surface. This will smooth the surface and reduces the etch rate per pulse.

In another preferred embodiment, the target tissue is kept reasonably hydrated, but not excessively so. When the target is dried, the etch rate per pulse increases and the surface roughness increases for the same ablation depth. The water acts as a smoothing agent by shielding target surface irregularities during the ablation.

In another preferred embodiment, the corneal surface is cooled to at or below 80° F. by placing a cold mask or by irrigation with a cold physiologic solution prior to commencing a photorefractive keratectomy. By reducing thermal (heat) side effects of the laser pulses, the surface smoothness is enhanced.

In another preferred embodiment, a scanning spot delivery system, such as used in the LaserSight, Inc. (Orlando, Fla.) LaserScan 2000, is used to remove a layer of tissues 1–2 microns thick; then the direction of the scan is rotated 60°–90° in order to achieve a photopolishing effect by smoothing the surface of each preceding scan layer.

In another preferred embodiment, the pattern of scan is randomized to reduce the production of a regularity that accentuates the tissue peaks. For example, each succeeding scan direction is rotated randomly from 30°–90°.

In another preferred embodiment, the pattern of pulse overlap is varied from 50%–80% in order to smooth the ablation surface wherein there is a linear increase in pulse overlap percentage as the pulse spot size decreases. That is to say, there is an inverse linear relationship between pulse size and pulse overlap. For any given pulse size, the percentage overlap is set to maximize ablation smoothness.

Figure 4B:
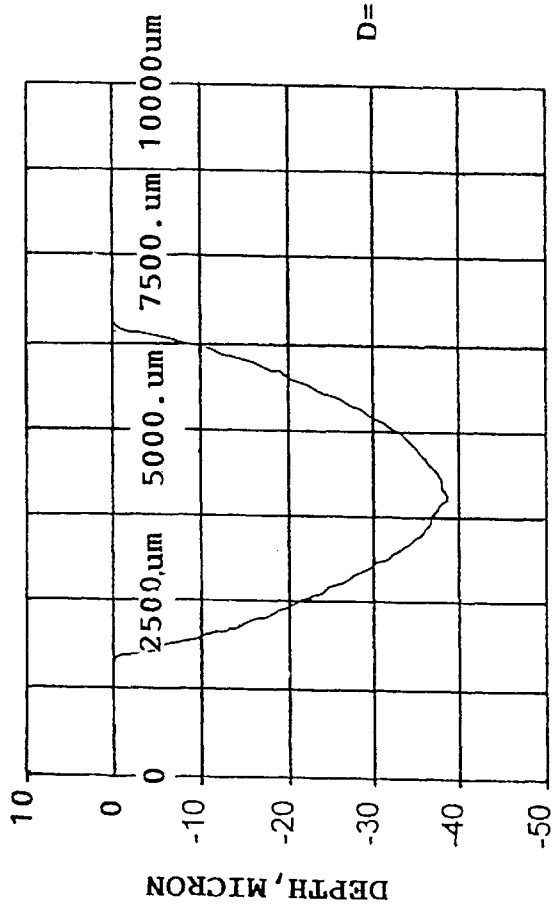
FIG. 4 provides (A) aspheric ablation profile that allows for a relatively shallow central ablation depth and hence a smoother ablation profile than (B) disclosing a spherical ablation profile, which is deeper and rougher in the center.
Figure 5A:
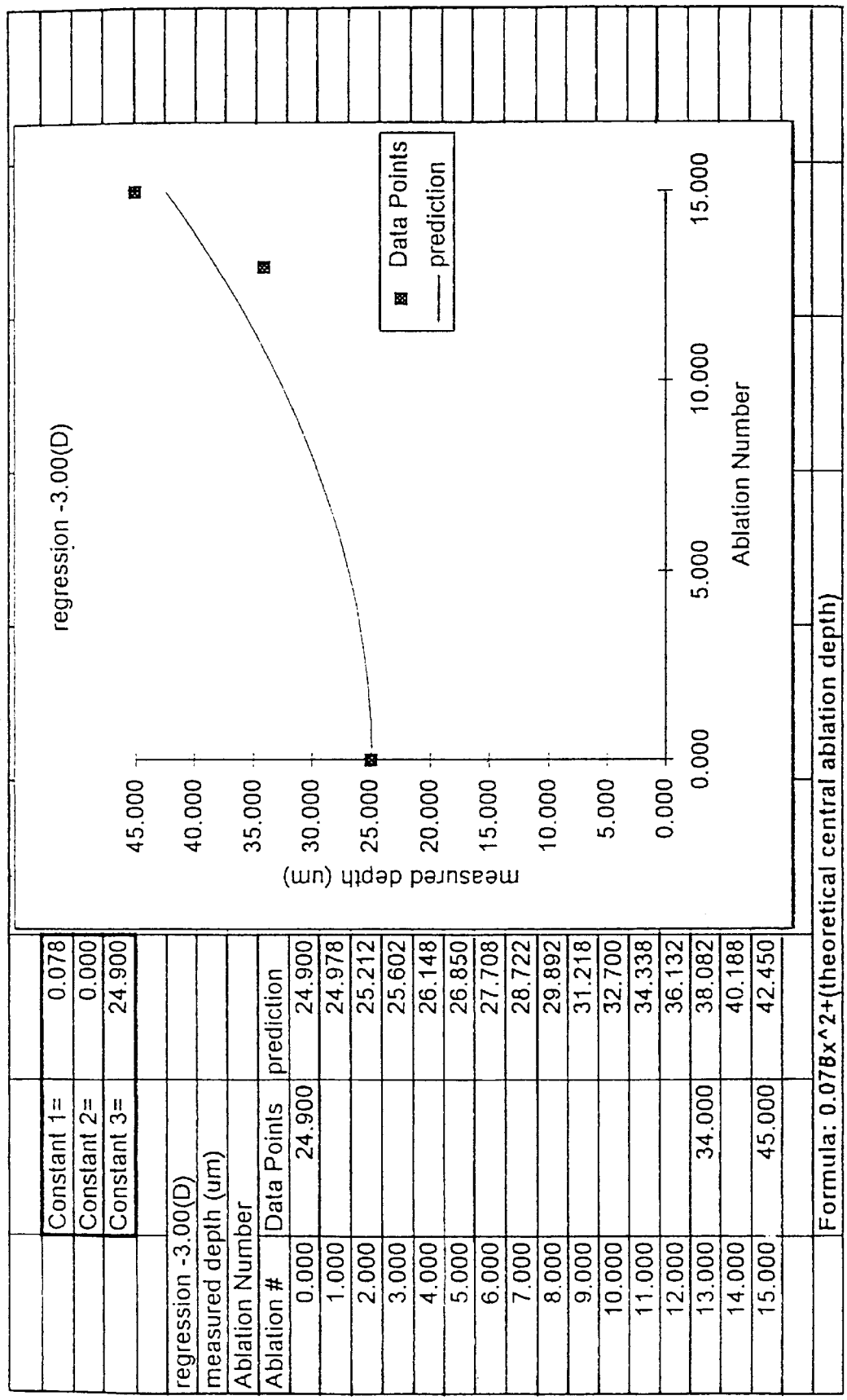
FIG. 5 discloses the nonlinear relationship between the RMS (nanometers) per micrometer of ablation in corneal tissue (adjusted from PMMA data) and the correction in cornea necessary to take into account the effects of regression for a 5 mm ablation zone. The best-fit plots for a three (3) diopter correction (A) and for a six (6) diopter correction (B) are demonstrated. For a perfectly smooth ablation with no regression (RMS=0), the corneal central ablation depth for a three-diopter correction is about 25 micrometers and for a six-diopter correction about 50 micrometers.
Figure 5B:
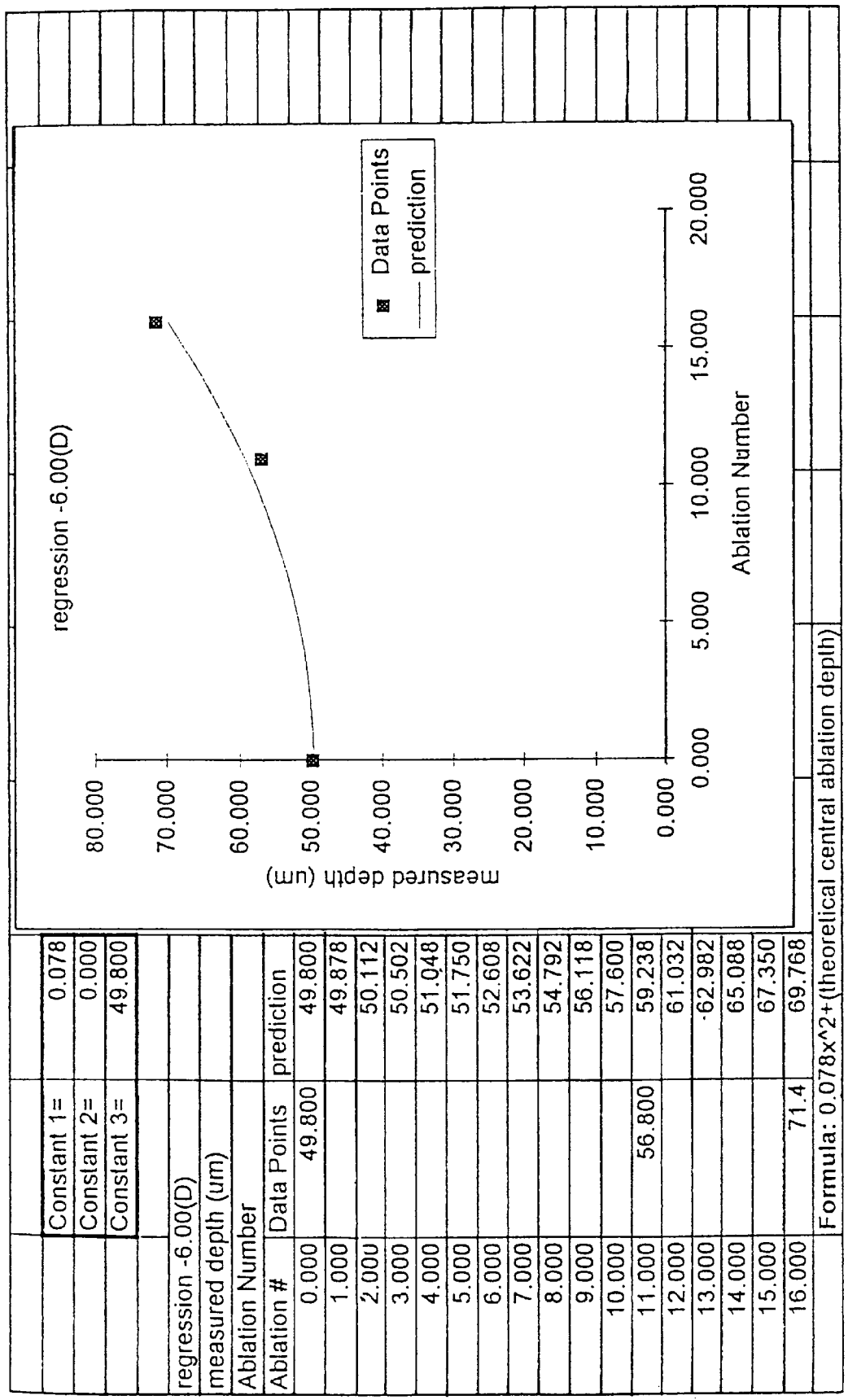

In another preferred embodiment, a variable aperture or scanning spot laser delivery system is used to create an aspheric ablation profile. By reducing central ablation depth, the ablation smoothness is improved (FIG. 4).

In another preferred embodiment, a contact lens is used immediately after the PRK, which molds the epithelial growth in order to enhance the ablation smoothness. After the epithelium has covered the defect created by the laser treatment, the contact lens can be discontinued. If subepithelial haze begins to appear, however, the contact lens can be replaced for temporary use to suppress haze and regression.

Variations or modifications to the subject matter of this invention may occur to those skilled in the art upon reviewing the invention herein. For example, the PRK variant know as LASIK is the laser refractive correction done under a corneal flap. Such variations or modifications, if within the spirit of this disclosure, are intended to be encompassed within the scope of this invention as set forth.

What is claimed is:

1. A method of improving ablation smoothness of a photorefractive keratectomy (PRK) procedure performed on the corneal eye surface of a patient comprising the steps of:

(a) performing an ablation with a laser on a simulated corneal surface;

(b) analyzing the ablation by surface profilemetry on the simulated corneal surface to determine if a resulting ablation smoothness, as root means square (RMS), is 15 nm per micron or less; and (c) performing a PRK procedure with the laser on the corneal surface eye of a patient if the determined ablation smoothness, as a root means square (RMS), is 15 nm per micron or less.

* * * * *